US005468234A

United States Patent [19]

Griffin et al.

[11] Patent Number: 5,468,234

[45] Date of Patent: Nov. 21, 1995

[54] APPARATUS AND METHOD FOR SHOWER PUVA TREATMENT

[75] Inventors: Edmond I. Griffin, Atlanta; Dolores A. Dehdashti, Smyrna, both of Ga.

[73] Assignee: Edmond I. Griffin, Atlanta, Ga.

[21] Appl. No.: 348,462

[22] Filed: Dec. 2, 1994

[51] Int. Cl.[6] .................................................. A61M 35/00

[52] U.S. Cl. .............................. 604/290; 604/289; 4/524; 601/156

[58] Field of Search .................................... 604/289–291; 601/156, 160, 166; 607/88, 91–95; 4/524–526

[56] References Cited

U.S. PATENT DOCUMENTS 3,868,950 3/1975 Kato ........................................ 601/156
4,724,553 2/1988 Bianchi .................................. 601/156

FOREIGN PATENT DOCUMENTS 23658 9/1899 United Kingdom ....................... 4/526

OTHER PUBLICATIONS

Vacuum and Pressure Systems, Gast Manufacturing Systems Benton Harbor, Mich. 49022, pp. 35–37, 1979.

*Primary Examiner*—Mary Beth Jones
*Assistant Examiner*—Mark O. Polutta
*Attorney, Agent, or Firm*—Hopkins & Thomas

[57] ABSTRACT

A shower PUVA apparatus has a reservoir within which a medicinal solution may be placed. The medicinal solution is pumped to a plurality of water jets which are positioned to uniformly coat the body with the medicinal solution. After coating the body, the medicinal solution is returned to the reservoir and recirculated throughout the apparatus. A water heater maintains the temperature of the medicinal solution at a constant temperature and a drape protects the head of the body from the spray of medicinal solution. The apparatus may be used for the treatment of psoriasis by uniformly coating the body with a psoralen solution. The treatment of psoriasis with the shower apparatus involves spraying a psoralen solution uniformly over the body of the patient for five minutes. The patient is then exposed to ultraviolet A light at an exposure determined by the skin type and a previous exposure to light.

18 Claims, 1 Drawing Sheet

APPARATUS AND METHOD FOR SHOWER PUVA TREATMENT

FIELD OF THE INVENTION

This invention generally relates to an apparatus and method for the treatment of psoriasis. More particularly, this invention relates to an apparatus and method for shower PUVA treatment of psoriasis.

BACKGROUND OF THE INVENTION

Psoriasis is a common skin disease characterized by marked changes in tissue architecture and by simultaneous activation of a variety of distinct cell types, including epidermal keratinocytes, vascular elements, and leukocytes. The clinical appearance of psoriasis includes red, raised, scaly plaques which are attributed to alterations in the growth and maturation in both the epidermis and dermis of the skin.

A conventional treatment of psoriasis is the oral administration of a psoralen followed by the application of ultraviolet A light (PUVA). A typical treatment using oral PUVA is the administration of eight-methoxypsoralen (8-MOP) followed by exposure to UVA light. Following a treatment, the patient would need to wear protective glasses for twenty-four hours.

A method of treatment preferred by some doctors over oral PUVA is bath PUVA. Bath PUVA involves the delivery of a photosensitizing drug, such as 8-MOP, to the skin followed by the exposure to UVA light. With bath PUVA, the patient soaks in psoralen solution for approximately thirty minutes and then receives an immediate exposure to a therapeutic dosage of UVA light. The patient may soak his or her entire body from the neck below into the psoralen solution, or alternatively, may soak only those portions of the body which are afflicted with psoriasis.

Bath PUVA has proven to be more effective and more pleasurable in treating psoriasis than oral PUVA. In comparison to oral PUVA, bath PUVA has been shown to require approximately one-half as many treatments and at a significantly lower dosage of UVA light. Because there is no systemic absorption of psoralen, bath PUVA does not cause nausea, fatigue, or depression as has been reported with oral PUVA. It reduces the potential for cataract formation, and reduces the possible risk of PUVA-induced cutaneous cancers. Additionally, with bath PUVA, the patient need not wear protective glasses for twenty-four hours after treatment. The effectiveness of oral PUVA is also limited by the body's ability to absorb the medicine from the gastrointestinal tract. In this regard, bath PUVA is preferred since it is not subject to the variances in the absorption of the medicine.

Bath PUVA therapy, however, is also subject to several disadvantages. A single treatment with bath PUVA is approximately three times more expensive than that for oral PUVA. Bath PUVA is also more expensive for the private practitioner since it requires the practitioner to purchase a bathtub and fill and clean the tub for each treatment. The effectiveness of a bath PUVA treatment is also dependent upon the temperature of the water, which is not easily controlled in the bathtub. The effectiveness of bath PUVA also varies due to differences in body size and shape, which prevent uniform coverage with the psoralen solution, and since the coverage of the upper shoulders, torso, and knees is difficult. Furthermore, many patients object to the bath PUVA treatment since it requires them to sit within the confines of a bathtub for thirty minutes with increasingly colder bath water.

SUMMARY OF THE INVENTION

One aspect of the invention relates to an apparatus for uniformly delivering a medicinal solution to a body. The apparatus comprises a reservoir for holding a medicinal solution and a pump for moving the solution from the reservoir to a plurality of water jets. The water jets are positioned such that the medicinal solution uniformly covers the body with a spray of the medicinal solution. The excess solution emitted from the water jets is returned back into the reservoir, thereby recirculating the medicinal solution.

In a preferred embodiment, the reservoir is a five gallon reservoir and a 2.5 gallon water heater maintains the temperature of the medicinal solution at a constant 105° F. A temperature sensor is installed in a return pipe for indicating the temperature of the psoralen solution emitted by the water jets. A wall mounted temperature gauge displays the water temperature. The head of the body is protected from the spray of medicinal solution by a drape. The application of the medicinal solution may be performed within an enclosure having a slanted floor designed to return the medicinal solution to the reservoir.

Another aspect of the invention relates to a method for uniformly delivering a medicinal solution to a body. The method comprises the steps of placing the medicinal solution within a reservoir and then pumping the medicinal solution to a plurality of water jets. The medicinal solution is emitted by the water jets to uniformly cover the body with the medicinal solution. After being emitted from the water jets, the medicinal solution flows back into the reservoir and is recirculated through the system.

Preferably, the method further comprises the steps of heating and regulating the temperature of the medicinal solution to a constant 105° F. The method may be performed within an enclosure and involves the step of protecting the head of the body from the spray of medicinal solution.

The apparatus and method of the invention may be used for the treatment of psoriasis by uniformly coating the body with a psoralen solution. The shower PUVA treatment is performed for five minutes two or three times a week until the skin is 95% clear. After each treatment, the medicinal solution is drained from the reservoir and a disinfectant is circulated through the system. The invention, however, is not limited to just the treatment of psoriasis, but is equally applicable to the treatment of other skin disorders or skin diseases.

DETAILED DESCRIPTION OF THE PREFERRED EMBODIMENT

Figure 1:
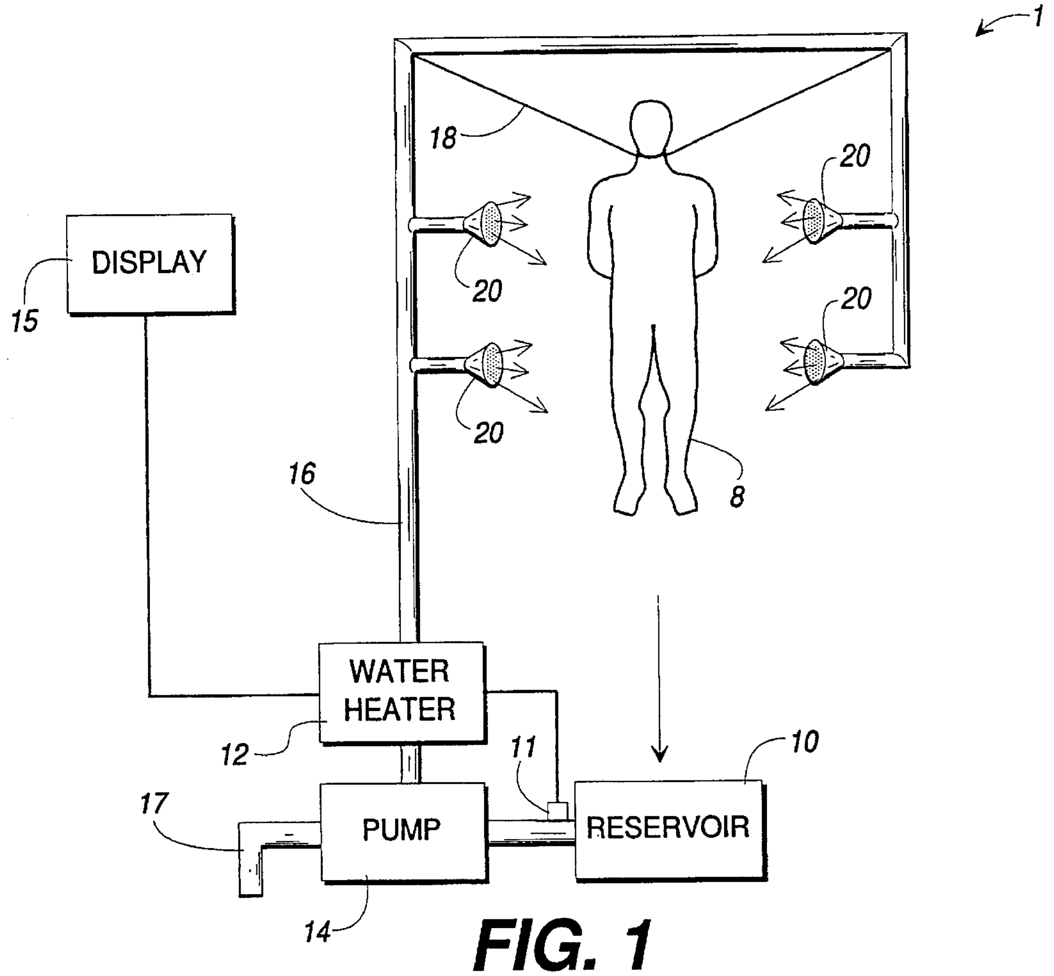
FIG. 1 is a block diagram of an apparatus according to a preferred embodiment of the invention.

The invention is generally related to an apparatus 1 and method for uniformly delivering a medicinal solution to a body. While the apparatus 1 is described below with reference to the treatment of psoriasis, the apparatus 1 may be used to treat other diseases, such as eczema or atopic dermatitis.

The apparatus 1 according to the invention comprises a reservoir 10 within which a psoralen solution is placed. A pump 14 delivers the psoralen solution from the reservoir 10 through a pipe 16 to a plurality of water jets 20. The water jets 20 are positioned to uniformly coat the body B with the psoralen solution. The psoralen solution is returned to the reservoir 10 and recirculated back to the water jets 20.

Preferably, the reservoir 10 is a five gallon stainless steel reservoir and the water heater 12 is an "IN-SYNKERATOR™" 2.5 gallon water heater that maintains the psoralen solution at a constant water temperature of 105° F. A temperature sensor 11 is mounted on a return pipe, such as a pipe between the reservoir 10 and the pump 14, for indicating a temperature of the psoralen solution emitted by the water jets 20. The temperature of the psoralen solution is displayed on a wall mounted temperature gauge 15. The pump 14 is a multi-stage centrifugal Grundos water pump that circulates the psoralen solution to the water heater 12, through the pipe 16, and to the water jets 20. After the psoralen solution has been emitted by the water jets 20 to uniformly coat the surface of the body B, the excess psoralen solution is returned to the reservoir 10.

Figure 2:
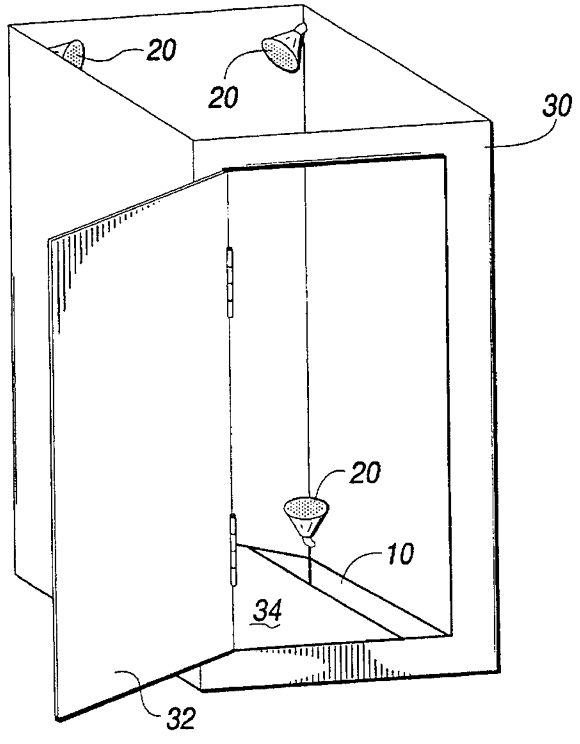
FIG. 2 is a perspective view of a shower enclosure.

With reference to FIG. 2, the psoralen solution is preferably applied to the surface of a body B within an enclosure 30. The enclosure 30 is preferably a tiled shower stall with a conventional glass door 32 and measures 52" long by 41" wide by 81" high. The enclosure 30 has an angled floor 34 for directing the excess psoralen solution back into the reservoir 10, which is formed in a recessed portion of the floor 34. The reservoir 10 preferably has a cover (not shown) which is mounted flush with the floor 34 and which has a plurality of apertures for the passage of the psoralen solution back into the reservoir 10. Alternatively, the reservoir 10 could be placed beneath the enclosure 30 with suitable plumping directing the excess psoralen solution back to the reservoir 10.

The shower jets 20 are preferably eight stainless steel adjustable water jets which are placed equally on the right and left walls of the enclosure 30. The water jets 20 may have both the angle at which the psoralen solution is ejected as well as the height of the spray adjusted. The drape 18 may comprise a disposable plastic drape which is suspended from the walls of the enclosure 30 using, for instance, rubber suction cup devices with hooks.

At the end of each treatment, the psoralen solution within the reservoir 10 is discharged through a pipe 17 by activating the pump 14. The psoralen solution could alternatively be discharged in other manners, such as by mounting a drain plug at the bottom of the reservoir 10 so that the psoralen solution can be sent directly to a discharge pipe. After the psoralen solution has been discharged from the system, a disinfectant is added to the reservoir 10 and the pump 14 is activated to circulate the disinfectant throughout the entire system. The disinfectant can then be discharged in the same manner as the psoralen solution.

A treatment with the shower PUVA apparatus 1 involves first dissolving a psoralen into 50 cc. of hot water. Preferably, the psoralen is 50 mg of OXSORALEN ULTRA™ which is then dissolved within the 50 cc. of hot water. To enhance absorption, other medicines may be added to the psoralen solution. For instance, 1 cc. of DMSO may be added to the 50 mg of OXSORALEN ULTRA™. This solution is then added to approximately five gallons of water within the reservoir 10.

A test for minimal phototoxic dose (MPD) is performed on each patient and read at 48 hours. The patient is then irradiated with, for instance, DERMALIGHT™ metal halide equipment using an H-1 filter at the MPD. If no MPD was obtained, the lowest test increment is the starting dose of UVA. The exposure is advanced in increments of 0.5 J for skin type I, 1.0 J for skin type II, 1.5 J for skin type III, and 2.0 J for skin type IV. The treatments are prescribed for two or three times per week, depending upon the skin type, until the patient is more than 95% clear, at which time the patient is placed on routine maintenance of one treatment per week for one month. After the one month maintenance treatment, all treatments are discontinued if the skin remains clear.

The treatment of psoriasis with the shower PUVA apparatus 1 is preferred over oral PUVA for many of the same reasons that bath PUVA is preferred over oral PUVA. For instance, the side effects associated with taking oral medication are eliminated, such as the nausea, fatigue, and depression. Also, the success of shower PUVA does not depend upon the ability to absorb the psoralen within the gastrointestinal tract. Further, the patients undergoing shower PUVA treatment need not wear protective glasses for twenty-four hours after the treatment.

The shower PUVA therapy also has advantages over bath PUVA. For instance, the psoralen solution is applied more evenly over the body of a patient in comparison to bath PUVA due to the size and weight differences of the patient. Shower PUVA also provides more consistent results since the temperature of the solution is maintained at a constant therapeutic temperature. A single treatment with shower PUVA is less expensive than bath PUVA given that the shower PUVA apparatus 1 uses approximately 19 liters of the psoralen solution whereas bath PUVA uses approximately 150 liters of psoralen solution. The costs of staffing an office are also less with shower PUVA since the preparation time and clean-up time is much less than that required for bath PUVA. Shower PUVA is also desirable since the treatment times are shorter, which allows a greater number of treatments during a day. Many patients prefer shower PUVA over bath PUVA since the treatment time for a shower PUVA is only five minutes in comparison to thirty minutes with bath PUVA and since the patients feel more comfortable in the shower than in the confines of the bathtub. The shower PUVA is also preferred since the water temperature is maintained at a constant warm temperature and since the shower both relaxes the patient and helps to debride the psoriasis, which increases the effectiveness of the UVA exposure.

During an initial trial for shower PUVA therapy, the average dosage of ultraviolet. A light required for clearing the skin was 24 Joules, and the total Joules during the treatment ranged from 225 Joules to 365 Joules. While the shower PUVA required an average of four additional treatments in comparison to oral PUVA, the patients preferred the shower PUVA over the oral PUVA treatments.

It will further be obvious to those skilled in the art that many variations may be made in the above embodiments, here chosen for the purpose of illustrating the present invention, and full result may be had to the doctrine of equivalents without departing from the scope of the present invention, as defined by the appended claims.

What is claimed is:

1. An apparatus uniformly delivering a psoralen solution to a body, comprising:

a reservoir containing said psoralen solution;

means for pumping said psoralen solution from said reservoir to a plurality of jettisoning means;

said jettisoning means positioned such that said psoralen solution emitted from said jettisoning means uniformly covers said body;

means for routing said psoralen solution emitted from said Jettisoning means back into said reservoir; and wherein said psoralen solution is recirculated during operation of said apparatus.

2. The apparatus as set forth in claim 1, further comprising means for heating said psoralen solution and regulating a temperature of said psoralen solution to an approximately constant temperature.

3. The apparatus as set forth in claim 1, further comprising a drape for protecting a head of said body from said psoralen solution emitted from said jettisoning means.

4. The apparatus as set forth in claim 1, further comprising a rectangular enclosure for containing said body and wherein said jettisoning means are positioned equally on walls of said enclosure.

5. The apparatus as set forth in claim 1, wherein said plurality of jettisoning means comprises a plurality of jets.

6. The apparatus as set forth in claim 1, wherein said pumping means comprises a multi-stage centrifugal pump.

7. The apparatus as set forth in claim 1, wherein said reservoir has a capacity of approximately five gallons.

8. A method for uniformly delivering a psoralen solution to a body, comprising the steps of:

placing psoralen solution within a reservoir;

pumping said psoralen solution from said reservoir to a plurality of jettisoning means;

emitting said psoralen solution with said jettisoning means such that said body is uniformly covered with said psoralen solution; and recirculating said psoralen solution emitted from said jettisoning means to said reservoir.

9. The method as set forth in claim 8, further comprising the steps of heating and regulating said psoralen solution to an approximately constant temperature before being emitted by said jettisoning means.

10. The method as set forth in claim 9, wherein said steps of heating and regulating said psoralen solution maintains said psoralen solution at said approximately constant temperature of 105° F.

11. The method as set forth in claim 8, further comprising the step of protecting a head of said body from said psoralen solution emitted from said jettisoning means.

12. The method as set forth in claim 8, further comprising the step of placing said body within a rectangular enclosure and placing said jettisoning means equally on walls of said enclosure.

13. The method as set forth in claim 8, wherein said step of emitting said psoralen solution comprises the step of emitting said psoralen solution for approximately 5 minutes.

14. The method as set forth in claim 13, further comprising the step of repeating said step of emitting said psoralen solution twice a week.

15. The method as set forth in claim 13, further comprising a step of sensitizing said body to a therapeutic dosage of ultraviolet light.

16. The method as set forth in claim 8, further comprising the steps of draining said psoralen solution and circulating a disinfectant after said body has been uniformly coated with said psoralen solution.

17. An apparatus for delivering a medicinal solution to a body, comprising:

a reservoir for holding a medicinal solution;

means for pumping said medicinal solution from said reservoir no a plurality of jettisoning means, said means for pumping positioned in communication with said reservoir and said jettisoning means;

said jettisoning means positioned such that said medicinal solution emitted from said jettisoning means contacts said body; and means for routing said medicinal solution comprising a floor located below said jettisoning means, said floor being angled so that at least a portion of the medicinal solution emitted from said jettisoning means is routed back into said reservoir;

wherein said medicinal solution is recirculated during operation of said apparatus.

18. An apparatus delivering a psoralen solution to a body, comprising:

a reservoir containing said psoralen solution;

means for pumping said psoralen solution from said reservoir to a plurality of jets, said means for pumping positioned in communication with said reservoir and said jets;

said jets positioned such that said medicinal solution emitted from said Jets contact said body; and means for routing at least a portion of said psoralen solution emitted from said jets back into said reservoir;

wherein said psoralen solution is recirculated during operation of said apparatus.

* * * * *